United States Patent [19]
Bhatnagar et al.

[11] Patent Number: 6,046,197
[45] Date of Patent: Apr. 4, 2000

[54] HEMOREGULATORY COMPOUNDS

[75] Inventors: Pradip Kumar Bhatnagar, Exton; Dirk Andries Heerding, Malvern; Stephen M. LoCastro, Exton, all of Pa.

[73] Assignee: Smithkline Beecham Corporation, Philadelphia, Pa.

[21] Appl. No.: 09/068,491

[22] PCT Filed: Nov. 12, 1996

[86] PCT No.: PCT/US96/18247

§ 371 Date: Nov. 23, 1998

§ 102(e) Date: Nov. 23, 1998

[87] PCT Pub. No.: WO97/18214

PCT Pub. Date: May 22, 1997

Related U.S. Application Data

[60] Provisional application No. 60/006,641, Nov. 3, 1995, and provisional application No. 60/015,537, Apr. 17, 1996.

[51] Int. Cl.[7] .................. A61K 31/495; C07D 487/04
[52] U.S. Cl. ........................... 514/249; 544/349
[58] Field of Search .............................. 544/349; 514/249

[56] References Cited

U.S. PATENT DOCUMENTS

| 4,499,081 | 2/1985 | Laerum et al. | 514/17 |
| 5,760,003 | 6/1998 | Bhatnagar et al. | 514/17 |

OTHER PUBLICATIONS

DeMarsh et al., J. Infect.Dis.,173,p. 203–211, 1996.
Pelus et al., Exp.Hematol.,22,p. 239–247, 1994.
DeMarsh et al., Immunopharmacology,27, p. 199–206, 1994.
Tomiyasu et al., Chemical Abstracts, vol. 97, No. 145258, 1982.

*Primary Examiner*—Emily Bernhardt
*Attorney, Agent, or Firm*—Linda E. Hall; Stephen A. Venetianer; Charles M. Kinzig

[57] ABSTRACT

The present invention relates to novel compounds which have hemoregulatory activities and can be used to stimulate hematopoiesis and for the treatment of viral, fungal and bacterial infectious diseases.

7 Claims, No Drawings

HEMOREGULATORY COMPOUNDS

This application claims the benefit of U.S. Provisional Application Nos. 60/006,641, filed Nov. 13, 1995 and 60/015,537, filed Apr. 17, 1996.

FIELD OF THE INVENTION

The present invention relates to novel compounds which have hemoregulatory activities and can be used to stimulate hematopoiesis and for the treatment of viral, fungal and bacterial infectious diseases.

BACKGROUND OF THE INVENTION

The hematopoietic system is a life-long cell renewal process whereby a defined stem cell population gives rise to a larger population of mature, differentiated blood cells (Dexter T M. Stem cells in normal growth and disease. Br Med J 1987; 195:1192–1194) of at least nine different cell lineages (erythrocytes, platelets, eosinophils, basophils, neutrophils, monocytes/macrophages, osteoclasts, and lymphocytes) (Metcalf D. The Molecular Control of Blood Cells. 1988; Harvard University Press, Cambridge, Mass.). Stem cells are also ultimately responsible for regenerating bone marrow following treatment with cytotoxic agents or following bone marrow transplantation.

The major dose-limiting toxicities of most standard antineoplastic drugs are related to bone marrow suppression, which if severe and prolonged, can give rise to life-threatening infectious and hemorrhagic complications. Myelosuppression is predictable and has been reported to be dose-limiting in greater than 50% of single-agent Phase I trials cytotoxic compounds (Merrouche Y, Catimel G, Clavel M. Hematopoietic growth factors and chemoprotectants; should we move toward a two-step process for phase I clinical trials in oncology? Ann Oncol 1993; 4:471–474). The risk of infection is directly related to the degree of myelosuppression as measured by the severity and duration of neutropenia (Brody G P, Buckley M, Sathe Y S, Freireich E J. Quantitative relationship between circulating leukocytes and infections with acute leukemia. Ann In Med 1965; 64:328–334).

The control of hematopoiesis involves the interplay of a variety of cytokines and growth factors during various stages of the hematopoietic cascade, including early pluripotent stem cells and mature circulating effector cells. These regulatory molecules include granulocyte colony stimulating factor (G-CSF), granulocyte-macrophage stimulating factor (GM-CSF), macrophage-colony stimulating factor (M-CSF), and a variety of interleukins which have overlapping, additive and synergistic actions which play major roles in host defense. Mechanistically, this is accomplished by enhancing the production of granulocytes and macrophages, as well as by the activation of effector cell functions (Moore M A S. Hemopoietic growth factor interactions: in vitro and in vivo preclinical evaluation. Cancer Surveys 1990; 9:7–80). These coordinated activities support optimal host defences which are necessary for fighting bacterial, viral and fungal infections.

Strategies to prevent or reduce the severity of neutropenia and myelotoxicity include the use of hematopoietic growth factors and/or other hematopoietic cytokines. Such treatments are becoming common practice, in that they offer the potential of increased doses of cytotoxic agents that may improve the therapeutic efficacy of antineoplastic agents, and reduce the morbidity associated with their use (Steward W P. Granulocyte and granulocyte-macrophage colony stimulating factors, Lancet 1993; 342:153–157). Clinical studies have demonstrated the G-, GM- and/or M-CSF may reduce the duration of neutropenia, accelerate myeloid recovery, and reduce neutropenia-associated infections and other infectious complications in patients with malignancies who are receiving cytotoxic chemotherapy or in high infectious-risk patients following bone marrow transplantation (Steward WP. Granulocyte and granulocyte-macrophage colony stimulating factors, Lancet 1993; 342:153–157 and Munn D H, Cheung N K V. Preclinical and clinical studies of macrophage colony-stimulating factor. Semin Oncol 1992; 19:395–407).

Synthetic peptides have been reported to induce the synthesis and release of hematopoietic mediators, including m-CSF from bone marrow stromal elements (see U.S. patent application Ser. No. 08/001,905).

We have now found certain novel non-peptide compounds which have a stimulative effect on myelopoietic cells. They are useful in stimulating myelopoiesis in patients suffering from reduced myelopoietic activity, including bone marrow damage, agranulocytosis and aplastic anemia including patients having depressed bone marrow function due to immunosuppressive treatment to suppress tissue reactions i.e. in bone marrow transplant surgery. They may also be used to promote more rapid regeneration of bone marrow after cytostatic chemotherapy and radiation therapy for neoplastic and viral diseases. They may be of particular value where patients have serious infections due to a lack of immune response following bone marrow failure. They are also useful in the treatment and prevention of viral, fungal and bacterial disease.

SUMMARY OF THE INVENTION

This invention comprises compounds, hereinafter represented as Formula (I), which have hemoregulatory activities and can be used to stimulate hematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopenia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animals. The compounds are also useful in the treatment and prevention of viral, fungal and bacterial infectious diseases, particularly Candida and Herpes in both immunosuppressed and "normal" subjects. They are useful in the treatment of sepsis caused by gram negative and gram positive organisms.

These compounds may also be used in combination with the myelosuppressive agents of co-pending U.S. application Ser. No. 07/799,465 and U.S. Pat. No. 4,499,081, incorporated by reference herein, to provide alternating peaks of high and low activity in the bone marrow cells, thus augmenting the natural circadian rhythm of hematopoiesis. In this way, cytostatic therapy can be given at periods of low bone marrow activity, thus reducing the risk of bone marrow damage, while regeneration will be promoted by the succeeding peak of activity.

This invention is also a pharmaceutical composition, which comprises a compound of Formula (I) and a pharmaceutically acceptable carrier.

This invention further constitutes a method for stimulating the myelopoietic system of an animal, including humans, which comprises administering to an animal in need thereof, an effective amount of a compound of Formula (I).

This invention also constitutes a method for preventing and treating viral, fungal and bacterial infections including sepsis in immunosuppressed and normal animals, including humans, which comprises administering to an animal in need thereof, an effective amount of a compound of Formula (I).

DETAILED DESCRIPTION OF THE INVENTION

The compounds of the invention are represented by structural Formula (I)

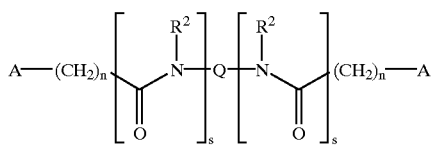

wherein:
A is

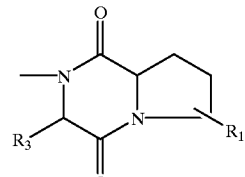

or

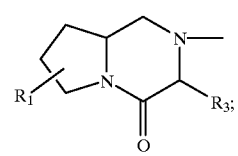

$R_1$ is independently $NH_2$, OH, SH, CN, $CO_2H$ or hydrogen;

$R_2$ is independently hydrogen, $C_{1-4}$ alkylC(O)$R_5$, $C_{1-4}$ alkyl or $R_2$ is benzyl which is optionally substituted by one or two $C_{1-4}$ alkyl, $C_{1-4}$ alkoxy, F, Cl, I, Br, OH, or N($R_4$)$_2$;

$R_3$ is independently hydrogen, $C_{1-5}$ alkyl, $C_{1-5}$ alkylenehydroxy, $C_{1-5}$alkyleneCO$_2$H, (CH$_2$)$_y$N(R$_4$)$_2$, (CH$_2$)$_m$ C(O)N(R$_4$)$_2$, $C_{1-5}$ alkyleneSH, CH$_2$Ar,

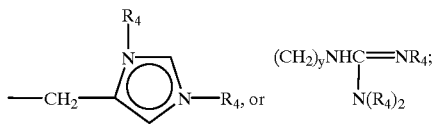

$R_4$ is independently hydrogen, $C_{1-5}$ alkyl or benzyl;

Ar is independently phenyl or indolyl optionally substituted by one or two $R_7$ groups;

Q is bicyclo[3.3.0]octanyl, xylyl, benzophenonyl or 1,2,3,4-tetrahydronapthalyl; all of which are unsubstituted or substituted by one or two substituents chosen from: $C_{1-4}$alkyl, $C_{1-4}$alkoxy, halogen, mono or di $C_{1-4}$alkylamino, ($C_{1-4}$alkyl)$_2$—NC(O)—, —(CH$_2$)$_n$—R$_5$, —(CH$_2$)$_n$—R$_6$, —(CH$_2$)$_n$—COR$_5$ or —(CH$_2$)$_n$—COR$_6$;

$R_5$ is —OR$_6$, —N(R$_6$)$_2$, or —SR$_6$;

$R_6$ is hydrogen, $C_{1-4}$ alkyl or benzyl;

$R_7$ is halogen, $R_5$ or $R_6$;

n is independently an integer from 0 to 3;

m is independently an integer from 1 to 3;

s is independently 0 or 1; and y is independently an integer from 2 to 4;

provided that n is not 0 when s is 1 and further provided that the compound of Formula (I) is not:

[(S),(S)]-N,N'-(1,4-xylenediyl)bis[2-acetamido-6,7,8,8a-tetrahydropyrrolo[1,2-α]pyrazine-1,4(2H, 3H)-dione];

[(R),(R)]-2,2'-(1,2-xylenediyl)bis[6,7,8,8a-tetrahydropyrrolo[1,2-α]pyrazine-1,4(2H,3H-dione]; or

[(S),(S)]-2,2'-(1,3-xylenediyl)bis[6,7,8,8a-tetrahydropyrrolo[1,2-α]pyrazine-1,4(2H,3H-dione];

or a pharmaceutically acceptable salt thereof.

This invention is also a pharmaceutical composition, which comprises a compound of Formula (I) and a pharmaceutically acceptable carrier.

Alkyl groups may be straight or branched. Halogen may be chloro, iodo, fluoro or bromo.

The compounds of the present invention may contain one or more asymmetric carbon atoms and may exist in racemic and optically active forms. All the compounds and diastereomers are contemplated to be within the scope of the present invention.

Preferred compounds of Formula (I) are those wherein $R_1$ is OH or hydrogen; $R_3$ is CH$_2$OH or hydrogen and Q is xylyl or bicyclo[3.3.0]octanoyl. More preferred compounds are those wherein $R_1$, $R_2$ and $R_3$ are hydrogen and Q is xylyl.

The most preferred compounds of the invention are:

[3(S),3'(S),8a(S),8a'(S)]-N,N'-(1,4-xylenediyl)bis[2-(acetamido)-3-(hydroxymethyl)-6,7,8,8a-tetrahydropyrrolo[1,2-α]pyrazine-1,4(2H, 3H)-dione] or

[(S),(S)]-2,2'-(1,2-xylenediyl)bis[6,7,8,8a-tetrahydropyrrolo[1,2-α]pyrazine-1,4(2H,3H-dione]

[(S),(S)]-2,2'-(1,2-xylenediyl)bis[6,7,8,8a-tetrahydropyrrolo[1,2-α]pyrazine-1(2H, 3H,4H)-one]

METHOD OF PREPARATION

Compounds of Formula (I) wherein A is tetrahydropyrrolopyrazinedione and $R_1$, $R_2$, $R_3$ and n are defined as in Formula (I) are prepared by methods analogous to those in Scheme 1.

Scheme 1

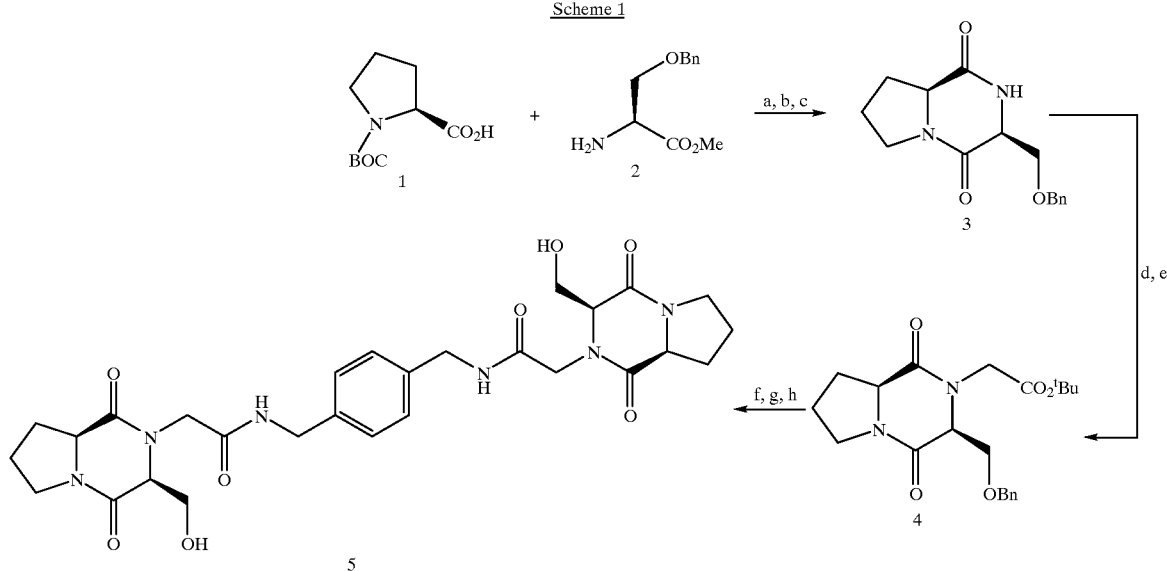

a) EDC, HOBt, iPr₂NEt, DMF; b) TFA, CH₂Cl₂; c) pTSOH, toluene, reflux;
d) NaH, THF; e) t-butyl bromoacetate; f) TFA, CH₂Cl₂; g) EDC, HOBt,
iPr₂NEt, DMF; h) anyhdrous HF Suitably protected amino acids (such as 1 and 2 in Scheme 1) are coupled using standard solution phase peptide synthesis methods (such as EDC, HOBt, iPr₂NEt in DMF) giving a protected dipeptide. Removal of the protecting group on nitrogen followed by cyclization using catalytic amounts of a mild acid (such as p-toluenesulfonic acid) in a suitable solvent (such as toluene) gives the diketopiperazine (such as 3 in Scheme 1). The diketopiperazines (such as 3 in Scheme 1) are alkylated with a suitably protected alkylating agent (such as t-butyl bromoacetate) in a suitable aprotic polar solvent (such as THF) to give the N-alkylated diketopiperazine (such as 4 in Scheme 1). Removal of the t-butyl ester under acidic conditions (such as TFA in CH₂Cl₂) followed by coupling to a suitable diamine (such as 1,4-xylylene-diamine) under standard conditions (such as EDC, HOBt and iPr₂NEt) in a suitable solvent (such as DMF) gives the protected, coupled product. Removal of the protecting groups under typical conditions (such as anhydrous HF) gives the final product (such as 5 in Scheme 1).

Scheme 2

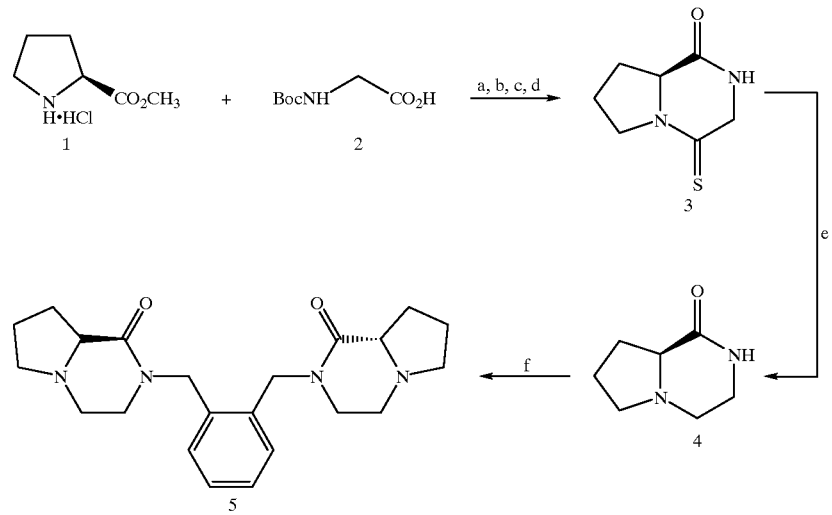

a) EDC, HOBt, iPr₂NEt, CH₂Cl₂; b) Lawesson's reagent, toluene; c) TFA, CH₂Cl₂; d) iPr₂NEt, toluene; e) Ra-Ni, MeOH; f) o-dibromoxylene, NaH, THF Compounds of Formula (I) wherein A is tetrahydropyrrolopyrazinone are prepared by methods analogous to those in Scheme 2. Suitably protected amino acids (such as 1 and 2 in Scheme 2) are coupled using standard solution phase peptide synthesis methods (such as EDC, HOBt, iPr$_2$NEt in CH$_2$Cl$_2$) to give the protected dipeptide. The amide group is converted to the thioamide using conventional reagents (such as Lawesson's reagent) in a suitable solvent (such as toluene) to give the corresponding protected thioamide. Removal of the protecting group on nitrogen followed by a thermally assisted ring closure gives the cyclic thioamide (such as 3 in Scheme 2). The thioamide is reduced using conventional reagents (such as Raney-Nickel) in a suitable polar solvent (such as MeOH) to give the tetrahydropyrrolopyrazinone (such as 4 in Scheme 2). Alkylating the sodium salt of this compound with one half an equivalent of a suitable dihalide (such as o-dibromoxylene) gives the final product (such as 5 in Scheme 2).

In order to use a compound of the Formula (I) or a pharmaceutically acceptable salt thereof for the treatment of humans and other mammals it is normally formulated in accordance with standard pharmaceutical practice as a pharmaceutical composition.

According to a still further feature of the present invention there are provided pharmaceutical compositions comprising as active ingredient one or more compounds of Formula (I) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such a glyceryl monostearate or glyceryl distearate, alone or with a wax. The amount of solid carrier varies but, preferably will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. Capsules containing one or several active ingredients may be produced, for example, by mixing the active ingredients with inert carriers, such as lactose or sorbitol, and filling the mixture into gelatin capsules. When a liquid carrier is used, the preparation will be in the form of a syrup, elixir, emulsion or an aqueous or non-aqueous suspension. Such a liquid formulation may be administered directly p.o. or filled into a soft gelatin capsule. Organ specific carrier systems may also be used.

Alternately pharmaceutical compositions of the compounds of this invention, or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

For rectal administration, a pulverized powder of the compounds of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.05–50 mg, for example 0.05–5 mg of the compound of formula (I) or salt thereof.

According to a still further feature of the present invention there is provided a method of stimulation of myelopoiesis which comprises administering an effective amount of a pharmaceutical composition as hereinbefore defined to a subject.

No unacceptable toxicological effects are expected when compounds of the invention are administered in accordance with the present invention.

The biological activity of the compounds of Formula (I) are demonstrated by the following tests.

Induction of Hematopoietic Synergistic Activity in Stromal Cells

The murine bone marrow derived stromal cell line, C6.4 is grown in 12 well plates in RPMI 1640 with 10% FBS. Upon reaching confluence, the C6.4 cells are washed and the media exchanged with fresh RPMI 1640 without FBS. Confluent cell layers of murine C6.4 cells are treated with compound. Cell-free supernatants are collected 18 hours later. Supernatants are fractionated with a Centricon-30 molecular weight cut-off membrane. C6.4 cell hematopoietic synergistic factor (HSF) activity is measured in a murine CFU-C assay.

CFU-C Assay

Bone marrow cells are obtained from C57B1/6 female mice and suspended in RPMI 1640 with 10% FBS. Bone marrow cells (7.5E+4 cells/mL) are cultured with sub optimal levels of CFU plus dilutions of test C6.4 cell 30K-E supernatants from above in a standard murine soft agar CFU-C assay. Cell aggregates >50 cells are counted as colonies. The number of agar colonies counted is proportional to the amount of HSF present within the C6.4 bone marrow stromal line supernatant.

Effector Cell Function Assay

Female C57B1 mice are administered test compound IP or PO daily for 8 days. Resident peritoneal exudate cells (PEC) utilized ex vivo from treated or untreated mice are harvested with cold calcium and magnesium-free DPBS supplemented with heparin and antibiotics within 2–4 hours following the last injection. Adherent PEM populations are prepared by incubating standardized PEC suspensions in microtiter dishes for 2 hours at 37° C. (5% CO$_2$) and removing nonadherent cells by washing the wells with warm buffer.

The superoxide dismutase-inhibitable (SOD) superoxide released by effector cells in response to a in vitro stimulation by phorbol myristate acetate (PMA) (100–200 nM) or pre-opsonized (autologous sera) live C. albicans (E:T=1:10) are quantitated in a microtiter ferricytochrome c reduction assay. The assay is performed in the presence of 1% gelatin/HBSS and 80 uM ferricytochrome c in a total volume of 200 uL/well. The nmoles of cytochrome c reduced/well is calculated from spectrophotometric readings (550 nm) taken following a 1 hour incubation at 37° C. (5% $CO_2$). The amount of SOD-inhibitable cytochrome c reduced is determined by the inclusion of wells containing SOD (200 U/well). Baseline superoxide release is determined in the absence of stimuli. Experimental data are expressed as a percentage of the control group.

The following examples are illustrative and are not limiting of the compounds of this invention.

EXAMPLE 1

[3(S),3'(S),8a(S),8a'(S)]-N,N'-(1,4-xylenediyl)bis[2-(acetamido)-3-(hydroxymethyl)-6,7,8,8a-tetrahydropyrrolo[1,2-α]pyrazine-1,4(2H, 3H)-dione]

a) [3(S), 8a(S)]-2-(tert-Butoxycarbonylmethyl)-3-(benzyloxymethyl)-6,7,8,8a-tetrahydropyrrolo[1,2-α]pyrazine-1,4(2H, 3H)-dione.

A stirred suspension of NaH (0.120 g, 60% dispersion in oil, 3.0 mmol) in dry THF (15 mL) under argon was cooled to 0° C. A solution of compound Pro-Ser(Bzl) diketopiperazine (0.82 g, 3.0 mmol) in anhydrous DMF (10 mL) was added via syringe and the mixture was stirred for 20 min. t-Butyl 2-bromoacetate (0.54 mL, 3.3 mmol) was added, the cooling bath was removed and the reaction was stirred for 5 h. Water (10 mL) was added to quench the reaction. The mixture was diluted with $H_2O$ (50 mL) and sat NaCl (50 mL) and then extracted with $CHCl_3$ (3×50 mL). The combined organic layers were washed with $H_2O$ (2×50 mL), dried over $MgSO_4$, filtered and concentrated in vacuo to a yellow solid. Purification by flash chromatography (2/98 MeOH/$CHCl_3$, silica gel) gave 1.10 g (94%) of the desired product. MS (ESI) m/z 389.2 ($MH^+$).

b) [3(S),3'(S),8a(S),8a'(S)]-N,N'-(1,4-Xylenediyl)bis[2-(acetamido)-3-(benzyloxymethyl)-6,7,8,8a-tetrahydropyrrolo[1,2-α]pyrazine-1,4(2H, 3H)-dione].

To a stirred solution of the compound of Example 1 (a) (1.1 g, 2.8 mmol) in $CH_2Cl_2$ (10 mL) was added neat TFA (10 mL). After 2 h, the mixture was concentrated in vacuo to an oil, then azeotroped 3 times with toluene to remove excess acid. This product was stored under high vacuum for 1 day to dry further and then used directly in the next step.

The compound obtained above was dissolved in DMF (10 mL). 1,4-Xylylenediamine (0.14 g, 1.0 mmol), $iPr_2NEt$ (1.75 mL 10.0 mmol), HOBt (0.31 g, 2.3 mmol) and BOP reagent (1.02 g, 2.3 mmol) were added sequentially and the reaction was stirred at room temperature for 18 h. The reaction mixture was added to a rapidly-stirred mixture of EtOAc (100 mL), 1N HCl (100 mL), and sat NaCl (100 mL). After stirring for 1 h, the phases were separated and the aqueous layer was extracted with fresh EtOAc (2×50 mL). The combined organic layers were washed with $H_2O$ (3×50 mL), dried over $MgSO_4$, filtered and concentrated in vacuo to a yellow oil. Purification by flash chromatography (20/80 MeOH/EtOAc, silica gel) gave 234 mg (31%) of the desired product as a white solid. MS (ESI) m/z 765.4 ($MH^+$).

c) [3(S),3'(S),8a(S),8a'(S)]-N,N'-(1,4-Xylenediyl)bis[2-(acetamido)-3-(hydroxymethyl)-6,7,8,8a-tetrahydropyrrolo[1,2-α]pyrazine-1,4(2H, 3H)-dione].

The compound of Example 1 (b) (26 mg, 45 μmol) was dissolved in p-cresol (0.5 mL) in a 50-mL Teflon HF reaction vessel fitted with a magnetic stirring bar. The vessel was chilled to −78° C. and evacuated by water aspirator. Anhydrous HF (ca. 5 mL) was condensed into the mixture. The reaction mixture was warmed to 0° C. and stirred for 45 min. The HF was then carefully removed under vacuum. The residue was taken up in $Et_2O$ (25 mL) and was extracted with 0.1% TFA in $H_2O$ (v/v, 4×25 mL). The combined aqueous extracts were washed with $Et_2O$ (3×25 mL) and then concentrated in vacuo to ca 10 mL. This solution was lyophilised to a white powder. Purification by HPLC [$CH_3CN/H_2O$ (0.1% TFA, Hamilton PRP-1] gave 6.3 mg (24%) of the title compound as a white powder. MS (ESI) m/z 585.2 ($MH^+$).

EXAMPLE 2

[(S),(S)]-2,2'-(1,2-xylenediyl)bis[6,7,8,8a-tetrahydropyrrolo[1,2-α]pyrazine-1,4(2H,3H)-dione]

To a stirred suspension of NaH (88 mg, 60% dispersion in oil, 2.2 mmol) in anhydrous DMF (5 mL) under argon was added Pro-Gly diketopiperazine (0.34 g, 2.2 mmol) in one portion (slight amount of foaming occurred). After 20 min, α, α'-dibromo-o-xylene (0.26 g, 1.0 mmol) was added and the reaction was stirred for 4 h at room temperature. Water (2 mL) was added to quench the reaction. The mixture was diluted with $H_2O$ (10 mL) and sat NaCl (50 mL), then extracted with $CHCl_3$ (4×50 mL). The combined organic layers were dried over $MgSO_4$, filtered and concentrated in vacuo to a clear oil. Purification by flash chromatography (2/98 MeOH/$CHCl_3$, silica gel) afforded 289 mg (70%) of the title compound as a glassy solid. MS (ESI) m/z 411.2 ($MH^+$).

EXAMPLE 3

[(S),(S)]-2,2'-(1,2-xylenediyl)bis [6,7,8,8a-tetrahydropyrrolo[1,2-α]pyrazine-1(2H, 3H,4H)-one]

a) N-(t-Butoxycarbonylaminothioacetyl)proline methyl ester

To Boc-Gly-Pro-OMe (2.78 g, 9.72 mmol) in toluene (200 mL) was added Lawesson's reagent (2.36 g, 5.83 mmol). The mixture was heated to reflux for 2 h, then allowed to cool to RT and concentrated under vacuum to give a yellow residue. Flash chromatography (30% EtOAc/hexanes, silica gel) gave 2.33 g (76%) of the desired compound as a yellow oil. This was homogeneous by TLC and $^1$H NMR analysis and was used without further purification.

b) (S)-6,7,8,8a-tetrahydroprolyl[1,2-α]pyrazine-1-one-4 (2H,3H)-thione.

To the compound of Example 3(a) (2.22 g, 7.35 mmol) in $CH_2Cl_2$ (35 mL) at 0° C. was added TFA (35 mL). The ice bath was removed and the solution was allowed to stir for 1 h. The solvent was removed under vacuum and the residue was azeotroped from toluene (3×20 mL). The residue was suspended in toluene (500 mL) and $iPr_2NEt$ (3.84 mL, 22.0 mmol) was added. The reaction was heated to reflux for 18 h and then allowed to cool to RT. The reaction mixture was washed with 1N HCl/brine (2×50 mL, 1:1 v/v) and the aqueous washes were back extracted with EtOAc (100 mL). The combined organic layers were concentrated to give 0.92 g (74%) of the desired material as a yellow solid. This material was homogeneous by TLC and $^1$H NMR and was used without further purification.

c) (S)-6,7,8,8a-tetrahydroprolyl[1,2-α]pyrazine-1(2H,3H, 4H)-one

To the compound of Example 3(b) (0.92 g, 5.41 mmol) in MeOH (180 mL) was added Ra-Ni (ca. 9 g of a 50% aqueous slurry). The mixture was heated to reflux for 2 h, cooled to room temperature and filtered through celite to remove the Ra-Ni. The filter cake was washed with EtOH and the combined filtrates were concentrated under vacuum to give 0.65 g (86%) of the desired material as pale yellow solid. This material was homogeneous by $^1$H NMR analysis and was used without further purification.

d) [(S),(S)]-2,2'-(1,2-xylenediyl)bis[6,7,8,8a-tetrahydropyrrolo[1,2-α]pyrazine-1(2H, 3H,4H)-one]

To the compound of Example 3(c) (0.65 g, 4.64 mmol) and o-dibromoxylene (0.55 g, 2.08 mmol) in THF (10 mL) was added NaH (0.19 g of a 60% dispersion in oil, 4.75 mmol) portionwise. The reaction was allowed to stir at RT for 24 h and then carefully poured into 1N HCl (75 mL). The aqueous phase was washed with hexane (20 mL) and Et$_2$O (20 mL). The combined organic phases were back extracted with 1N HCl (20 mL) and the combined aqueous phases were concentrated under vacuum to give a yellow residue. Reverse phase flash chromatography (step gradient, 100% H$_2$O+0.1% TFA; 5% CH$_3$CN/H$_2$O+0.1% TFA; 10% CH$_3$CN/H$_2$O+0.1% TFA; YMC reverse phase silica gel) gave 0.04 g of the title compound as a white solid. MS(ES+) m/z 383.1 (MH$^+$).

EXAMPLE 4

Formulations for pharmaceutical use incorporating compounds of the present invention can be prepared in various forms and with numerous excipients. Examples of such formulations are given below.

| Tablets/Ingredients | Per Tablet |
| --- | --- |
| 1. Active ingredient (Cpd of Form. I) | 0.5 mg |
| 2. Corn Starch | 20 mg |
| 3. Alginic acid | 20 mg |
| 4. Sodium alginate | 20 mg |
| 5. Mg stearate | 1.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

We claim:

1. A compound of Formula (I):

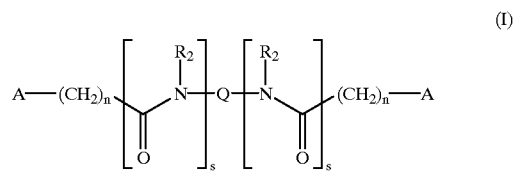

wherein:

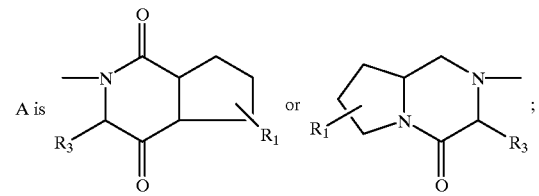

A is $R_1$ is independently hydrogen, NH$_2$, OH, SH, CN, CO$_2$H or hydrogen;

$R_2$ is independently hydrogen, C$_{1-4}$ alkylC(O)R$_5$, C$_{1-4}$ alkyl or R$_2$ is benzyl which is optionally substituted by one or two C$_{1-4}$ alkyl, C$_{1-4}$ alkoxy, F, Cl, I, Br, OH, or N(R$_4$)$_2$;

$R_3$ is independently hydrogen, C$_{1-5}$ alkyl, C$_{1-5}$ alkylenehydroxy, C$_{1-5}$alkyleneCO$_2$H, (CH$_2$)$_y$N(R$_4$)$_2$, (CH$_2$)$_m$ C(O)N(R$_4$)$_2$, C$_{1-5}$ alkyleneSH, CH$_2$Ar,

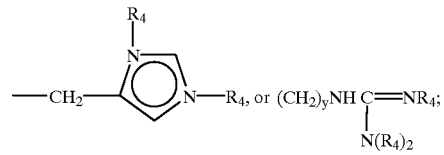

$R_4$ is independently hydrogen, C$_{1-5}$ alkyl or benzyl;

Ar is independently phenyl or indolyl optionally substituted by one or two R$_7$ groups;

Q is bicyclo[3.3.0]octanyl, xylyl, benzophenonyl or 1,2,3,4-tetrahydronaphthyl; all of which are unsubstituted or substituted by one or two substituents chosen from: C$_{1-4}$alkyl, C$_{1-4}$alkoxy, halogen, mono or di C$_{1-4}$alkylamino, or —(CH$_2$)$_n$—COR$_6$;

$R_5$ is —OR$_6$, —N(R$_6$)$_2$, or —SR$_6$;

$R_6$ is hydrogen, C$_{1-4}$ alkyl or benzyl;

$R_7$ is halogen, R$_5$ or R$_6$;

n is independently an integer from 0 to 3;

m is independently an integer from 1 to 3;

s is independently 0 or 1; and y is independently an integer from 2 to 4;

provided that n is not 0 when s is 1 and further provided that the compound of Formula (I) is not:

[(S),(S)]-N,N'-(1,4-xylenediyl)bis[2-acetamido-6,7,8,8a-tetrahydropyrrolo[1,2-α]pyrazine-1,4(2H, 3H)-dione];

[(R),(R)]-2,2'-(1,2-xylenediyl)bis[6,7,8,8a-tetrahydropyrrolo[1,2-α]pyrazine-1,4(2H,3H-dione]; or

[(S),(S)]-2,2'-(1,3-xylenediyl)bis[6,7,8,8a-tetrahydropyrrolo[1,2-α]pyrazine-1,4(2H,3H-dione];

or a pharmaceutically acceptable salt thereof.

2. A compound of claim 1 wherein R$_1$ is OH or H; R$_3$ is CH$_2$OH or H; and Q is xylyl or bicyclo[3.3.0.]octanyl.

3. A compound of claim 1 wherein $R_1$, $R_2$ and $R_3$ are hydrogen and Q is xylyl.

4. A compound of claim 1 which is:

[3(S),3'(S),8a(S)]-N,N'-(1,4-xylenediyl)bis[acetamido)-3-(hydroxymethyl)-6,7,8,8a-tetrahydropyrrolo[1,2-α]pyrazine-1,4(2H,3H)-dione] or

[(S),(S),2,2'-(1,2-xylenediyl)bis[6,7,8,8a-tetrahydropyrrolo[1,2-α]pyrazine-1,4(2H,3H-dione]

[(S),(S),2,2'-(1,2-xylenediyl)bis[6,7,8,8a-tetrahydropyrrolo[1,2-α]pyrazine-1(2H,3H, 4H)-one].

5. A method of preventing or treating bacterial infections which comprises administering to an animal in need thereof, an effective amount of a compound of claim 1.

6. A method of preventing or treating sepsis which comprises administering to an animal in need thereof, an effective amount of a compound of claim 1.

7. A process for preparing a compound of claim 1 which comprises:

a) For compounds wherein A is tetrahydropyrrolopyrazinedione, coupling two equivalents of a compound of Formula (II):

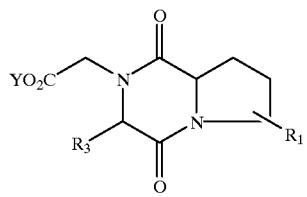

(II)

in which $R_1$ and $R_3$ are as defined in claim 1 or a group convertible thereto by removal of a protecting group; with a suitable diamine of Formula (IV):

(IV)

in which $R_2$ and Q are as defined in claim 1; with a coupling agent in a suitable solvent and removing any protecting groups; or b) For compounds wherein A is tetrahydropyrrolopyrazinone, alkylating a compound of Formula (V):

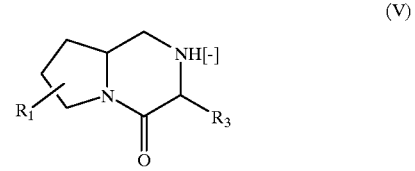

(V)

wherein $R_1$ and $R_3$ are as defined in claim 1 or a group convertible thereto by removal of a protecting group, with one half equivalent of a suitable dihalide of Formula (VI):

(VI)

in which X is Cl, F or I and Q is defined in Formula (I), followed if necessary by:

i) removing any protecting groups; and/or ii) salt formation.

* * * * *